US005643564A

United States Patent [19]

Hamaguchi et al.

[11] Patent Number: 5,643,564

[45] Date of Patent: Jul. 1, 1997

[54] GLYCOSYLATED CYTOKINES

[75] Inventors: Naoru Hamaguchi, Osaka; Jun Sato, Kawanishi; Kazuhiro Doken, Osaka, all of Japan

[73] Assignee: Takeda Chemical Industries, Ltd., Osaka, Japan

[21] Appl. No.: 455,661

[22] Filed: May 31, 1995

Related U.S. Application Data

[63] Continuation of Ser. No. 124,868, Sep. 22, 1993, abandoned.

[30] Foreign Application Priority Data

| | | | |
|---|---|---|---|
| Sep. 24, 1992 | [JP] | Japan | 4-254962 |
| Apr. 15, 1993 | [JP] | Japan | 5-088920 |

[51] Int. Cl.[6] .......... A61K 38/70; A61K 38/21; C07K 14/54; C07K 14/555

[52] U.S. Cl. .......... 424/85.1; 424/85.2; 424/85.4; 514/8; 514/12; 514/894; 530/351; 530/395; 530/402; 530/411

[58] Field of Search .......... 424/85.1, 85.2, 424/85.4, 85.7; 530/351, 395, 402, 410, 411; 435/811; 514/8, 12, 898, 894

[56] References Cited

U.S. PATENT DOCUMENTS

| | | | |
|---|---|---|---|
| 4,609,546 | 9/1986 | Hiratani | 424/83 |
| 4,829,690 | 5/1989 | Pestka et al. | 530/351 |
| 4,902,502 | 2/1990 | Nitecki et al. | 424/83 |
| 5,096,816 | 3/1992 | Maiorella | 435/70.21 |
| 5,162,503 | 11/1992 | Bailon et al. | 530/380.2 |

FOREIGN PATENT DOCUMENTS

| | | |
|---|---|---|
| 0063373 | 10/1982 | European Pat. Off. . |
| 0236987 | 9/1987 | European Pat. Off. . |
| 0251304 | 1/1988 | European Pat. Off. . |
| 1102098 | 4/1989 | Japan . |
| 1102099 | 4/1989 | Japan . |
| 3106900 | 5/1991 | Japan . |
| 211099 | 8/1992 | Japan . |
| 7-70195 | 3/1995 | Japan . |
| 88/02756 | 4/1988 | WIPO . |

OTHER PUBLICATIONS

Takenaga et al., "Galactose–conjugated Interferon Alpha", *Drug Delivery System*, vol. 8(5), p. 382, Sep. 1993.

Yoshito Ohtsubo et al., "Hepatic Targeting of Proteins Utilizing Carbohydrate Recognition Mechanism" Drug Delivery System, vol. 6, No. 1, Jan. 1991 (original Japanese and English translation).

Yuan Chuan Lee et al., "2–Imino–2–methoxyethyl 1–Thiglycosides: New Reagents for Attaching Sugars to Proteins", Biochemistry, vol. 15, No. 18, (1976) pp. 3956–3963.

Lee et al. Biochemistry 21(24): 6292–6298 1982.

Lee et al. "Further Studies on the Binding Characteristics of Rabbit Liver Galactose/N–Acetylgalactosamine–Specific Lectin " Biochemistry 21(24):6292–6298, 1982.

*Primary Examiner*—Mindy Fleisher
*Assistant Examiner*—Nancy J. Degen
*Attorney, Agent, or Firm*—Foley & Lardner

[57] ABSTRACT

Disclosed is a sugar-modified cytokine which ensures migration of almost all of the dose of cytokine to the liver rapidly after administration to the live body and which can be advantageously used to enhance the effect of liver disease therapy and mitigate side effects.

39 Claims, 5 Drawing Sheets

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Cys Tyr Cys Gln
1

( 2 ) INFORMATION FOR SEQ ID NO:2:

( i ) SEQUENCE CHARACTERISTICS:
( A ) LENGTH: 5 amino acids
( B ) TYPE: amino acid -continued ( C ) STRANDEDNESS: single
( D ) TOPOLOGY: linear ( i i ) MOLECULE TYPE: peptide ( x i ) SEQUENCE DESCRIPTION: SEQ ID NO:2:

```
Cys Tyr Cys Gln Asp
1               5
```

GLYCOSYLATED CYTOKINES

This application is a continuation of application Ser. No. 08/124,868, filed Sep. 22, 1993, now abandoned.

FIELD OF THE INVENTION

The present invention relates to a sugar-modified cytokine useful as a pharmaceutical.

BACKGROUND OF THE INVENTION

With the recent advances in biotechnology, a large number of cytokines have been isolated and purified. Also, as their mass production has become possible, they are now expected as candidate substances for new pharmaceuticals. However, many problems remain to be solved before such expectation is realized, among which is the development of a targeting drug delivery system for the desired cytokine. To strictly control cytokine behavior in vivo is assumed to be a key to enhancement of therapeutic effects and mitigation of side effects.

For example, interferon, a kind of cytokine, is a protein possessing diverse bioactivities such as antiviral activity and cell growth inhibition. For this pharmacological action, interferon is used to treat a large number of diseases, particularly chronic active hepatitis B and C and renal cancer. However, because interferon hardly migrates to the liver when administered to the live body and because it is quickly excreted from the body, it is difficult to maintain an effective concentration of interferon in the liver. For this reason, in order for the treatment of liver disease to be effective, high-dose long-term therapy is necessary, which involves the risk of side effects.

Concerning the mechanism of action of interferon in hepatitis, a mechanism of action of interferon-α in chronic active hepatitis C, for instance, is reported. Interferon reportedly acts directly on virus-infected hepatocytes to activate intrahepatocytic 2',5'-oligoadenylate synthetase (2–5AS) to produce 2',5'-oligoadenylate, which in turn activates RNase to lyse the viral-derived RNA, thus inhibiting protein synthesis and hence suppressing hepatitis C virus proliferation [Barson, S.: Tex. Res. Bio. Med., Vol. 35, 1 (1977)].

Five types of hepatitis virus, namely types A through E, have been discovered so far, among which is RNA type hepatitis C virus (HCV), whose gene was found in post-transfusion non-A, non-B hepatitis patient serum and against which there is no effective therapy. Hepatitis C is characterized by onset of acute symptoms and frequent chronic manifestation in adults. Although this chronic hepatitis progresses slowly, spontaneous healing occurs very rarely, with liver cirrhosis or hepatoma occurring in many cases. On the other hand, mass production of interferons has become possible, and these proteins have been shown to exhibit antiviral activity in vitro against HCV-related RNA type virus [Yasuyuki Ninomiya et al.: Clinical Report, 19, 231 (1985)] and to have a prophylactic effect against virus-infected mice [M. Kramer et al.: J. Interferon Res., 3, 425 (1983)], leading to expectation for their clinical effect on hepatitis C. Actually, recombinant interferon-α and -β have an excellent therapeutic effect on hepatitis C patients [J. H. Hoofnagle, et al.: N. Eng. J. Med., 315, 1575 (1986)], making possible positive approach toward the treatment of chronic hepatitis, which tends to be negative; they are now widely used clinically [Masami Yamanaka et al.: Journal of the Japanese Society of Internal Medicine, 79, 1037 (1990); Sadashi Shoji et al.: Japanese Journal of Gastroenterology, 88, 706 (1991)].

However, the efficacy rate of interferon in hepatitis C remains unsatisfactory, at most 40% [S. Kakuma et al.: Am. J. Gastroenterol., 85, 655 (1990); Hepatitis Study Group, KAN TAN SUI/Journal of Liver, Gall-bladder and Pancreas, 22, 491 (1991)]. In particular, in cases of high viral contents, such as patients of the HCV II genotype, the efficacy rate is not higher than 20% [K. Yoshioka et al.: Hepatology, 16, 293 (1982)]. It may therefore be possible to improve the efficacy rate in these cases by increasing the dose or extending the administration period. Also, almost no effect is expected from the present levels of interferon dose and administration period in cases where chronic hepatitis less progressed to liver cirrhosis.

When intravenously, intramuscularly or subcutaneously administered, interferon hardly migrates to the liver, the target organ, since interferon has a short half-life in the blood. Considerable doses of interferon are therefore required. Side effects of interferon include flu-like symptoms with fever, headache and general malaise and decrease in leukocytes and platelets in the initial stage, sustained slight fever, anorexia, insomnia and tendency toward depression in the intermediate stage, and alopecia and thyroid hypofunction in the last stage. For this reason, even in those patients who should be dosed with a sufficient interferon for a considerable period of time to obtain the desired drug effect, medication should be discontinued or the dose should be lowered upon onset of such side effects.

Meantime, Japanese Patent Unexamined Publication No. 152393/1988 suggests that polyethylene glycol derivatives having a sugar chain can be used to modify cytokines, and that the resulting modified protein can be used to increase the cytokine sustainability in vivo or to improve cytokine delivery to particular cells or tissue. Also, Japanese Patent Unexamined Publication No. 211099/1992 describes a glycosyl-protein derivative useful as a carrier for selective drug delivery to the bone marrow or brain. However, none of these publications disclose any sugar-modified cytokine useful in selective cytokine delivery to the liver.

Otsubo et al. reported that a kind of sugar-modified protein migrates to the liver and is digested in intracellular lysozyme [Drug Delivery System, Vol. 6, 13–17 (1991)]. However, no disclosure is given as to hepatic orientation of sugar-modified cytokine.

SUMMARY OF THE INVENTION

An object of the present invention is to provide a sugar-modified cytokine which ensures migration of almost all of the dose of cytokine to the liver rapidly after administration to the live body and which can be advantageously used to enhance the effect of liver disease therapy and mitigate side effects.

As a result of intensive investigation of how to rapidly migrate cytokine to the liver, the present inventors found that cytokine can be rapidly migrated to the liver by modifying it with a sugar or a sugar chain.

Accordingly, the present invention provides a sugar-modified cytokine which comprises binding a modifying group to at least one primary amino group of a cytokine, wherein said modifying group is represented by the formula (I):

$$R—X— \quad (I)$$

wherein R represents a glycosyl group;

X represents

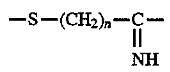

wherein n is an arbitrary positive integer,

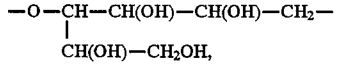

$-C_6H_4-NH-CS-$, $-S-CH_2-CO-NH-CH_2-CH_2-$, $-O-CH_2-CH_2-$, $-CS-NH-C_6H_3(CH_3)-NHCS-$, $-CO-(CH_2)_l-CO-$ wherein l is an integer of 3 to 6, $-CO-CH(OH)-CH(OH)-CO-$,

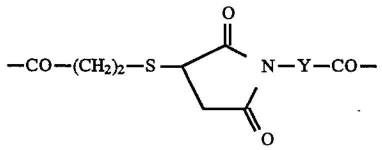

wherein Y is $-(CH_2)_3-$, 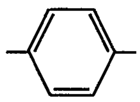 or 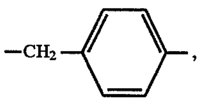,

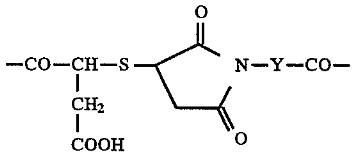

wherein Y is of the same meaning as mentioned above, $-CO-NH$, or

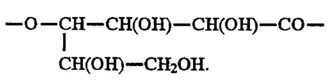

DETAILED EXPLANATION OF THE INVENTION

Figure 1:
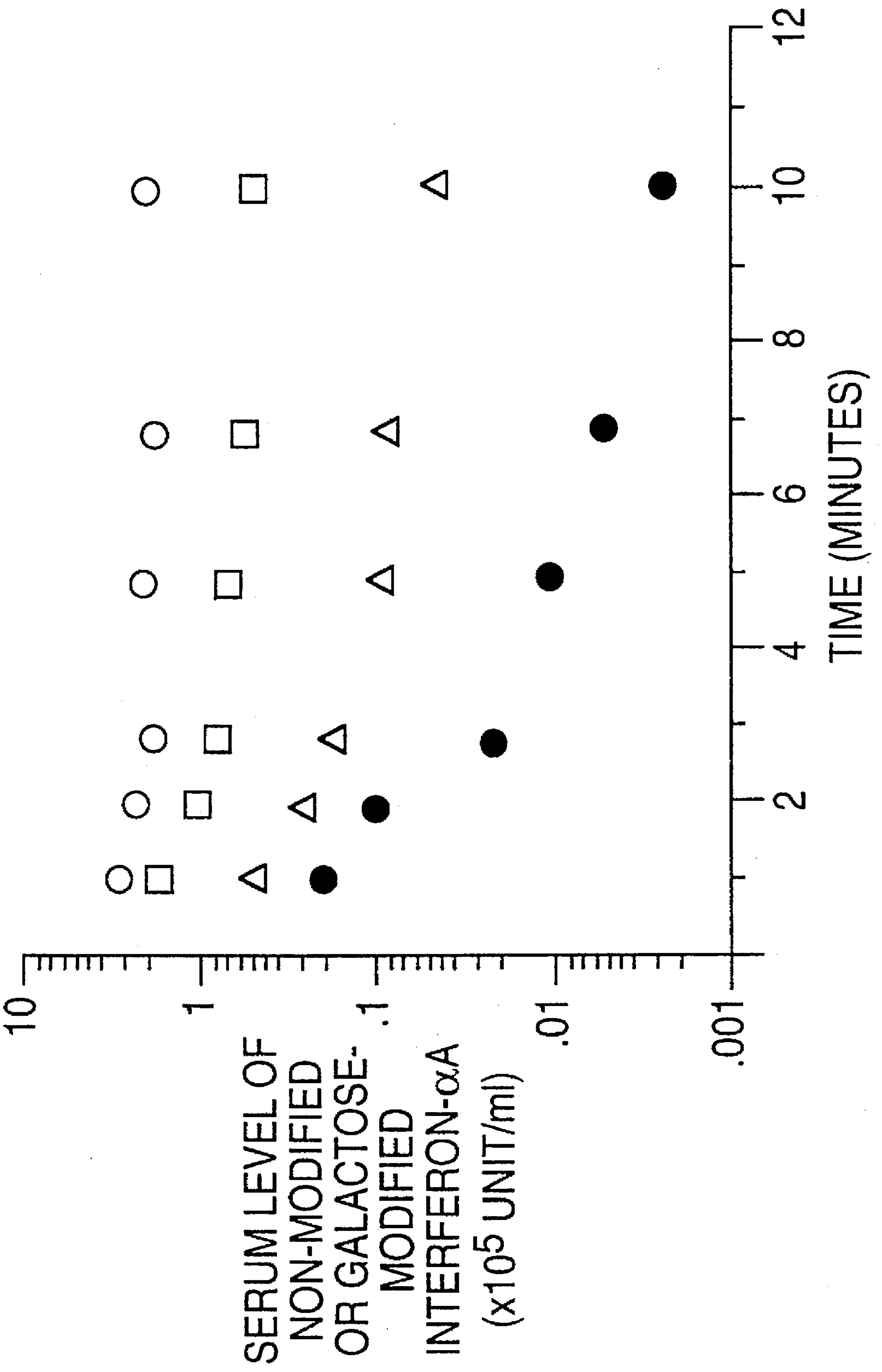
FIG. 1 shows the results of monitoring changes over time in serum level of non-modified or galactose-modified interferon-αA following intravenous administration of $3\times10^6$ units in rats. ○, □, Δ and ● show non-modified interferon-αA, the galactose-modified interferon-αA obtained in Example 16, the galactose-modified interferon-αA obtained in Example 3 and the galactose-modified interferon-αA obtained in Example 1, respectively.

Example of cytokines for the present invention include interleukin-1, which is obtained by activating macrophages with antigen, interleukin-2, which is obtained by activating T cells with antigen, interleukin-3, which is produced by particular clones of T cells, interleukin-4, T cell replacement factor (TRF) or B cell differentiation factor (BCDF), antigen-specific suppressor factor (TsF), soluble immune response suppression factor (SIRF), suppressor induction factor (SIF) and interferon-γ (IFN-γ), which are produced by T cells, B cell growth factor (BCGF), B cell differentiation enhancement factor (BCDF) and B cell growth suppression factor (SBF), which are produced by B cells, macrophage-activating factor (MAF), macrophage migration inhibition factor (MIF) and leukocyte migration inhibition factor (LIF), which are reportedly produced by B cells or T cells, interferon-α (IFN-α), granulocyte colony-stimulating factor (G-CSF), macrophage colony-stimulating factor (GM-CSF) and monocyte colony-stimulating factor (M-CSF), which are produced by macrophages etc., and interferon-β (IFN-β), which is produced by fibroblasts. Examples also include other interleukins such as interleukin-5 and interleukin-6, chemotactic factors such as macrophage chemotactic factor (MCF) and lymphocyte chemotactic factor (LCF), inflammatory lymphokines such as vascular permeability factor (VPF), perforin, which is produced by cytotoxic T cells, and tumoricidal factors such as lymphocyte-derived lymphotoxin (LT). The cytokine may also be a cell growth factor, exemplified by platelet-derived cell growth factor (PDGF), whose main targets are fibroblasts and smooth muscle cells, epidermal growth factor (EGF), whose main targets are fibroblasts, smooth muscle cells, vascular endothelial cells, epithelial cells and cartilage cells, fibroblast growth factor (FGF), whose main targets are fibroblasts, smooth muscle cells, vascular endothelial cells and epithelial cells, nerve growth factor (NGF), whose main target is nerve cells, nerve growth factors (IGF-I and IGF-II), whose main target is cartilage cells, erythropoietins, which proliferate erythrocytes, and hepatotropin (HTP) and hepatocyte growth factor (hHGF), which enhance hepatocyte growth.

Of the cytokines mentioned above, interferon (also referred to as IFN) or interleukin-2 (also referred to as IL-2) is preferable for the present invention. IFN may be of the α type, β type or γ type, with preference given to the α type.

The IFN-α is not subject to limitation, as long as it is a peptide substance possessing IFN-α activity or antiviral activity. For example, the IFN-α may be naturally occurring IFN-α or IFN-α obtained by gene engineering technology, with preference given to the latter. IFN-α obtained by gene engineering technology is exemplified by rIFN-αA, B, C, D, E, F, G, H, I and J (Japanese Patent Unexamined Publication No. 79897/1982 and European Patent Publication No. 43980). The IFN-α may be a derivative, as long as the essential activity is retained. Such derivatives include IFN-αA derivatives wherein the N-terminal amino group is acylated by —$COCH_3$ or —$COCH_2OH$ (Japanese Patent Unexamined Publication No. 41500/1988).

The IFN-γ is not subject to limitation, as long as it is a peptide substance possessing IFN-γ activity, i.e., antiviral activity, and immune system activating activity. For example, it may be naturally occurring IFN-γ or IFN-γ obtained by gene engineering technology, with preference given to the latter. Examples of IFN-γ obtained by gene engineering technology include those obtained by the method described in Japanese Patent Unexamined Publication No. 90514/1983 and those obtained by the method described in Japanese Patent Unexamined Publication No. 186995/1984. Also, the IFN-γ includes derivatives thereof, as long as the essential activity is retained.

Also, the interferon may be a mutein resulting from a change in its partial amino acid composition by deletion or replacement with other amino acids. In the case of IFN-γ, such muteins include fragments lacking one to several amino acids from the amino terminal and/or carboxyl terminal. Such fragments include those resulting from deletion of $Cys^1$-$Tyr^2$-$Cys^3$ at the N-terminal of IFN-γ and one to 17 amino acids or peptides from the C-terminal of the peptide chain from Gly 130 to Gln 146 at the C-terminal of the IFN-γ (Japanese Patent Unexamined Publication No. 202899/1985), partial sequences of IFN-γ comprising the amino acid sequence 5–127, 1–127 or 5–146 (Japanese Patent Unexamined Publication No. 233100/1985), those resulting from deletion of Cys-Tyr, Cys-Tyr-Cys or Cys-Tyr-Cys-Gln (SEQ. ID NO: 1) at the N-terminal of IFN-γ and one to 16 amino acids or peptides from the C-terminal of the peptide chain from Lys 131 to Gln 146 at the C-terminal of the IFN-γ (Japanese Patent Unexamined Publication No. 5096/1986), a partial sequence of IFN-γ comprising the amino acid sequence 1–131 (Japanese Patent Unexamined Publication No. 63295/1986), partial sequences of IFN-γ comprising the amino acid sequence 1–132 or 1–133 [Arakawa et al.: J. Biol. Chem., 261, 8534 (1986)], a partial sequence of IFN-γ comprising the amino acid sequence 1–135 (The Third Annual International Congress for Interferon Research), those resulting from deletion of $Cys^1$-$Tyr^2$-$Cys^3$-$Gln^4$-$Asp^5$ (SEQ ID NO: 2) at the N-terminal of IFN-γ and 0 to 19 amino acids or peptides from the C-terminal of the peptide chain from Lys 128 to Gln 146 at the C-terminal of the IFN-γ (Japanese Patent Unexamined Publication No. 99399/1987) and those resulting from deletion of Cys-Tyr-Cys or Cys-Tyr-Cys-Gln (SEQ ID NO: 1) at the N-terminal of IFN-γ and 18 to 25 peptides from the C-terminal of the peptide chain from Glu 122 to Gln 146 at the C-terminal of the IFN-γ (Japanese Patent Unexamined Publication No. 264500/1988).

The IL-2 may be a peptide substance, as long as it possesses activity similar to that of IL-2, exemplified by substances allowing subculture of T cells while maintaining their function. Specifically, it may be polypeptide (I) (human IL-2) having the amino acid sequence shown in FIG. 1 of Japanese Patent Unexamined Publication No. 78799/1986 (equivalent to European Patent Publication No. 176,299) or a fragment thereof comprising a partial amino acid sequence essential to the biological or immunological activity thereof. Such fragments include those resulting from deletion of one amino acid (EPC Publication No. 91539) or four amino acids (Japanese Patent Unexamined Publication No. 126088/1985) from the amino terminal of polypeptide (I), and those resulting from deletion of several amino acids from the carboxyl terminal. The fragment may also be one wherein one or more constituent amino acids of polypeptide (I) have been lacked or replaced by other amino acids, e.g., one wherein the cysteine residue at the position 125 has been replaced by a serine residue (Japanese Patent Unexamined Publication No. 93093/1984, equivalent to U.S. Pat. No. 4,518,584).

In particular, in the present invention, it is preferable to use a human IL-2 having the amino acid sequence shown in FIG. 1 of Japanese Patent Unexamined Publication No. 78799/1986 (equivalent to EPC Publication No. 176,299). In this case, the human IL-2 may be a mixture of one having an additional methionine residue (Met) at the amino terminal and another one lacking it (Japanese Patent Unexamined Publication Nos. 115528/1985 and 78799/1986), or one having no Met at the amino terminal and starting with alanine (Ala) (Japanese Patent Unexamined Publication No. 78799/1986).

Primary amino groups of cytokine include the α-amino acid of the N-terminal amino acid or the ε-amino group of a lysine residue.

With respect to the above formula (I), X is preferably represented by

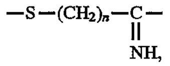

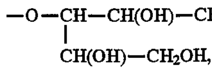

or

—$C_6H_4$—NH—CS—, more preferably

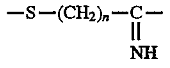

Also, the arbitrary positive integer for n in the above formula (I) is preferably not more than 10, more preferably 1 to 3.

The glycosyl group in formula (I) of the present invention may be a monosaccharide or polysaccharide. Such glycosyl groups include glycofuranosyl, glycopyranosyl and glycoseptanosyl groups, with preference given to the glycopyranosyl group.

Examples of the monosaccharide include groups comprising aldohexose such as the galactopyranosyl group, mannopyranosyl group, glucopyranosyl group and fucopyranosyl group, groups comprising hexosamine such as the 2-amino-2-deoxygalactopyranosyl group, 2-amino-2-deoxymannopyranosyl group, 2-amino-2-deoxyglucopyranosyl group and 2-amino-2-deoxyglucopyranosyl group, and groups comprising a hexosamine derivative such as the 2-acetamide-2-deoxygalactopyranosyl group, 2-acetamide-2-deoxymannopyranosyl group, 2-acetamide-2- deoxyglucopyranosyl group and 2-acetamide-2-deoxyfucopyranosyl group. Preferable monosaccharides are the galactopyranosyl group, mannopyranosyl group, 2-acetamide-2-deoxygalactopyranosyl group and 2-acetamide-2-deoxymannopyranosyl group, with greater preference given to the galactopyranosyl group and 2-acetamide-2-deoxygalactopyranosyl group.

The polysaccharide may be any one, as long as it has a monosaccharide as described above as a terminal component unit monosaccharide (non-reduced terminal), and the component monosaccharides other than the terminal monosaccharide may be any ones, as long as they are capable of forming polysaccharides. Also, the glycoside bond between monosaccharides may be of the α- or β-type. In this context, the terminal component unit monosaccharide of the glycosyl group comprising a polysaccharide is a component unit monosaccharide on the side opposite to the bond. For example, in the case of a polysaccharide having a galactopyranosyl group as a terminal monosaccharide, the polysaccharide is a galactopyranosyl-glycosyl group. In the case of a polysaccharide having a 2-acetamide-2-deoxygalactopyranosyl group as a terminal monosaccharide, the polysaccharide is a (2-acetamide-2-deoxygalactopyranosyl)-glycosyl group.

In the sugar-modified cytokine of the present invention, the modifying group having a sugar chain binds to a primary amine of the cytokine. The primary amine is exemplified by the α-amino group of the N-terminal amino acid or the ε-amino group of a lysine residue.

In the sugar-modified cytokine of the present invention, the sugar chain and the cytokine can be chemically bound by a known method of modification. A method of producing the sugar-modified cytokine of the present invention is as follows:

(a) reacting the compound represented by the formula

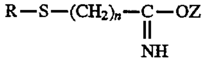

wherein R and n are of the same meaning as mentioned above and Z is a lower alkyl (e.g. methyl, ethyl, propyl, butyl) with a cytokine, (b) reacting the compound represented by the formula

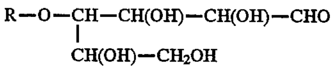

wherein R is of the same meaning as mentioned above with a cytokine, (c) reacting the compound represented by the formula $$R—C_6H_4—N=C=S$$

wherein R is of the same meaning as mentioned above with a cytokine, (d) reacting the compound represented by the formula $$R—S—CH_2—CO—NHCH_2—CHO$$

wherein R is of the same meaning as mentioned above with a cytokine, (e) reacting the compound represented by the formula $$R—O—CH_2—CHO$$

wherein R is of the same meaning as mentioned above with a cytokine, (f) reacting the compound represented by the formula

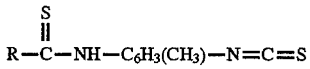

wherein R is of the same meaning as mentioned above with a cytokine, (g) reacting the compound represented by the formula $$R—CO—(CH_2)_l—CHO$$

wherein R and l are of the same meaning as mentioned above with a cytokine, (h) reacting the compound represented by the formula

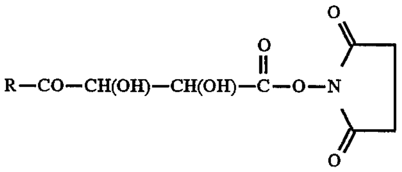

wherein R is of the same meaning as mentioned above with a cytokine, (i) reacting the compound represented by the formula $$R—CO—(CH_2)_2—SH$$

wherein R is of the same meaning as mentioned above with a maleimidated cytokine

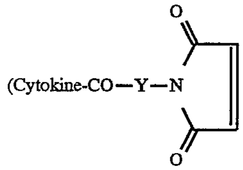 wherein Y is $—(CH_2)_3—$,

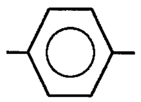 or 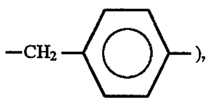 ), (j) reacting the compound represented by the formula

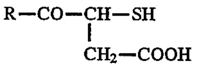

wherein R is of the same meaning as mentioned above with a maleimidated cytokine

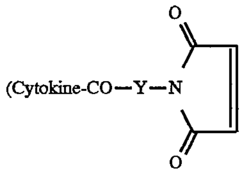

wherein Y is $-(CH_2)_3-$,

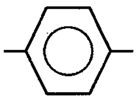

or

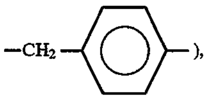

(k) reacting the compound represented by the formula

R—COOH wherein R is of the same meaning as mentioned above with a cytokine, or (l) reacting the compound represented by the formula $$R-O-CH(CH(OH)-CH_2OH)-CH(OH)-CH(OH)-COOH$$

wherein R is of the same meaning as mentioned above with a cytokine.

For example, in accordance with the method of Lee et al., the cyanomethyl-1-thioglycoside of the above-mentioned monosaccharide is reacted in methanol in the presence of sodium methoxide to yield 2-imino-2-methoxyethyl-1-thioglycoside, an active intermediate. This active intermediate is then reacted with the cytokine to bind amino acid residues of the cytokine, mainly amino functional groups, via an imide bond, to yield the desired sugar-modified cytokine [Biochemistry, Vol. 15, 3956–3963 (1976)]. Also, using a cyanoalkyl-1-thioglycoside such as cyanoethyl-1-thioglycoside or cyanopropyl-1-thioglycoside, as well the above-mentioned cyanomethyl-1-thioglycoside, the desired sugar-modified cytokine can be obtained. Even when the sugar is a polysaccharide, the desired sugar-modified cytokine can be obtained in accordance with the above-mentioned method of Lee et al.

When X is represented by $$-O-CH(CH(OH)-CH_2OH)-CH(OH)-CH(OH)-CH_2-$$

the sugar chain and cytokine can be chemically bound to modify the cytokine by, for example, a method wherein lactose, a disaccharide comprising galactose and glucose, is reductively aminated with cyanoborohydride to bind it with a primary amino group on the cytokine molecule [B. A. Schwartz et al.: Arch. Biochem. Biophys., 181,542 (1977); L. Flume et al.: FEBS Lett., 146, 42 (1982)]. Also, even when R is non galactose, the sugar-modified cytokine of the present invention can be obtained in accordance with this method.

When X is represented by $$-C_6H_4-NH-CS-$$

the sugar chain and cytokine can be chemically bound to modify the cytokine by, for example, a method wherein isothiocyanatophenyl β-galactopyranoside is coupled with a primary amino group on the cytokine molecule. [M. Monsigny et al.: Biol. Cell, 51, 187 (1984)]. Also, even when R is non galactose, the sugar-modified cytokine of the present invention can be obtained in accordance with this method.

When X is represented by $$-S-CH_2-CO-NH-CH_2-CH_2-$$

the sugar chain and cytokine can be chemically bound to modify the cytokine in accordance with the method described in R. T. Lee & Y. C. Lee: Biochem., 19, 156 (1980).

When X is represented by $$-O-CH_2-CH_2-$$

the sugar chain and cytokine can be chemically bound to modify the cytokine in accordance with the method described in J. Bogwald et al.: Carbohydr. Res., 148, 101 (1986).

When X is represented by $$-CS-NH-C_6H_3(CH_3)-NHCS-$$

the sugar chain and cytokine can be chemically bound to modify the cytokine in accordance with the method described in J. C. Rogers & S Kanfeld: Biochem. Biophys. Res. Commun., 45, 622 (1971).

When X is represented by $$-CO-(CH_2)_n-CO-$$

the sugar chain and cytokine can be chemically bound to modify the cytokine in accordance with the method described in S. Avrameas et al.: Immunochem., 6, 43 (1969) or M. Tiemeyer et al.: J. Biol. Chem., 264, 1671 (1989).

When X is represented by $$-CO-CH(OH)-CH(OH)-CO-$$

the sugar chain and cytokine can be chemically bound to modify the cytokine in accordance with the method described in J. Biol. Chem., 261, 205 (1986).

When X is represented by

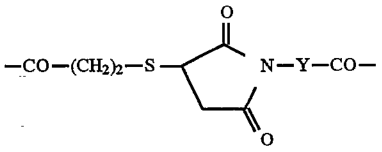

the sugar chain and cytokine can be chemically bound to modify the cytokine in accordance with the method described in E. Ishikawa et al.: J. Immunoassay, 4, 209 (1983).

When X is represented by

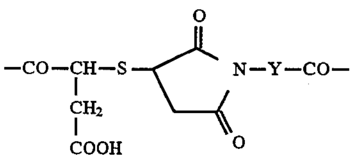

the sugar chain and cytokine can be chemically bound to modify the cytokine in accordance with the method described in E. Ishikawa et al.: J. Immunoassay, 4, 209 (1983).

When X is represented by $-CO-NH-$ or

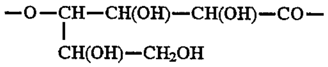

the sugar chain and cytokine can be chemically bound to modify the cytokine in accordance with the method described in B. F. Erlanger: Methods in Enzymology, 70, 85 (1981) or G. W. Anderson et al.: J. Am. Chem. Soc., 85, 1493 (1964).

When the starting material cytokine has an N-terminal amino group as the only primary amino group, the sugar-modified cytokine for the present invention has a group represented by formula (I) on said amino group. When one or more lysine residues are present in the cytokine, one or more ε-amino groups thereof, preferably about 5 to 80% (average), more preferably about 10 to 50% (average) of the ε-amino groups have a group represented by formula (I). In this case, the N-terminal α-amino group may or may not have a group represented by formula (I). For example, when the cytokine is interferon-α, the number of modifying groups represented by the formula (I) is preferably 1 to 9 molecules, more preferably 2 to 5 molecules, and still more preferably 4 molecules per interferon-α molecule. Also, when the cytokine is interleukin-2, the number of modifying groups represented by the formula (I) is preferably 1 to 8 molecules, more preferably 2 to 5 molecules per interleukin-2 molecule. The degree of modification can be adjusted by changing the molar ratio of modifying groups to the cytokine in the above reaction or by changing the reaction concentrations of the cytokine and modifying groups. The degree of modification can be quantitatively determined by the sulfuric acid-phenol method [J. F. McKelvy and Y. C. Lee: Arch. Biochem. Biophys., 132, 99 (1969)] and/or amino acid analysis.

The solvent used for the reaction of cytokine and a modifying group having a sugar or a sugar chain is not subject to limitation, as long as it does not interfere with the reaction. Such solvents include buffers such as phosphate buffers, borate buffers, Tris buffers and acetate buffers. Also, organic solvents such as lower alkanols (e.g., methanol, ethanol, isopropanol), acetonitrile, dimethylsulfoxide and dimethylformamide may be added, as long as they do not inactivate the cytokine or interfere with the reaction. Although reaction pH can be selected over a wide range of from about 3 to 14, weak alkalinity between pH about 7 and 9 is desirable. The degree of modification of the sugar-modified cytokine can also be adjusted by changing reaction pH. Although reaction temperature may be any one, as long as it does not result in cytokine denaturation, it is preferable to set it between about 0° C. and 40° C. Reaction time is about 3 to 72 hours, with satisfactory results obtained in about 24 to 30 hours of reaction. The reaction broth may be purified to the desired sugar-modified cytokine by ordinary protein purification methods such as dialysis, salting-out, ultrafiltration, ion exchange chromatography, gel filtration, high performance liquid chromatography and electrophoresis.

Since the higher-order structure of cytokine is important to the expression of its bioactivities, the sugar-modified cytokine of the present invention possesses useful bioactivities as do the corresponding non-modified cytokine, and is modified so that preferably over 60%, more preferably over 80% bioactivities are retained.

The bioactivities of cytokines modified with sugar chains can be assessed by various methods. For example, when the cytokine is an interferon, its antiviral activity can be assessed in vitro by the technique in which MDBK (Madin and Darby bovine kidney) cells are infected with VSV (vesicular stomatitis virus) and cultured in the presence or absence of the interferon, after which the cytopathic effect (CPE) is determined by the Neutral Red method [M. Rubinstein et al.: Proc. Natl. Acad. Sci. USA, 76, 640 (1979); R. K. Maheshwari and R. M. Friedman: Virol., 101, 399 (1980)]. Also, the effect on 2–5AS activity can be determined in accordance with a conventional method, using a commercially available 2–5A kit (Eiken Chemical Co., Ltd.). Furthermore, in liver targeting experiments in vivo, blood and tissue interferon concentrations in subject animals can be determined by a known immunoassay method (W082/01773) or the above-described antiviral activity test or 2,5-AS activity test.

The sugar-modified cytokine of the present invention is characterized by quicker elimination from the serum and quicker migration to the liver, in comparison with the corresponding known non-modified cytokine.

The sugar-modified cytokine of the present invention can be administered orally or non-orally to mammals (e.g., monkeys, dogs, swines, rabbits, mice, rats, humans) in the form of appropriate pharmaceutical compositions (e.g., capsules, injectable solutions), along with known carriers, diluents and other additives.

The sugar-modified cytokine of the present invention offers a therapeutic effect at low doses because it is efficiently transported to the target organ. With this feature, the sugar-modified cytokine of the present invention has few side effects such as fever and chilling and low toxicity, and can therefore be used more safely for the same purposes as with known non-modified cytokines by similar methods.

For example, the sugar-modified recombinant interferon-γ (rIFN-γ) of the present invention is used as a pharmaceutical for antiviral, antitumoral action and cell growth inhibition and immunopotentiation. In this case, it is administered by intravenous or intramuscular injection at a daily dose of 100,000 to 100,000,000 units rIFN-γ in each adult.

The sugar-modified recombinant interferon-αA (rIFN-αA) of the present invention is used as a pharmaceutical for antitumoral or antiviral therapy. In this case, it can be injected to the patient at a dose of about (0.1 to 10)$\times10^5$ units/day as of rIFN-αA.

For example, when it is intravenously injected to adult human patients with hepatitis B or C, it is used in an amount of about (0.1 to 100)$\times10^5$ units as rIFNαA daily, preferably about (0.5 to 30)$\times10^5$ units as rIFNαA daily.

The sugar-modified recombinant interleukin-2 (rIL-2) of the present invention is used as a pharmaceutical for antitumoral therapy. In this case, it can be injected to the patient at a dose of about (0.01 to 1.0)×400,000 units/day as of rIL-2.

When administered to mammals, the sugar-modified cytokine of the present invention disappears from the serum much more quickly and migrates to the liver more quickly, in comparison with non-modified cytokine. Moreover, the sugar-modified cytokine of the present invention mostly migrates to the liver, while non-modified cytokine hardly migrates to the liver. The sugar-modified cytokine of the present invention can therefore be advantageously used to enhance the effect of liver disease therapy.

The present invention is hereinafter described in more detail by means of the following working examples and experimental examples, which are not to be construed as limitative.

Example 1

1.0 g of cyanomethyl 2,3,4,6-tetra-o-acetyl-1-thio-β-D-galactopyranoside, the cyanomethyl thioglycoside of galactose, was dissolved in 25 ml of methanol. To this solution was added 48.5 μl of sodium methoxide (28% in methanol solution, produced by Wako Pure Chemical Industries), followed by a reaction at room temperature for 48 hours with stirring. A 5 ml portion of this methanol solution was dispensed to an egg-shaped flask, and the methanol was thoroughly evaporated using an evaporator (SIBATA, BUCHI RE111). To the resulting dry reaction product 2-imino-2-methoxyethyl-1-thio-β-D-galactopyranoside was added 1 ml of recombinant interferon-αA (rIFN-αA), at 3.3 mg/ml, pH 8.2 (0.1M phosphate buffer). After a reaction at room temperature for 24 hours, 100 μl of a 1M aqueous acetic acid solution was added to terminate the reaction. The unreacted galactopyranoside was removed using a gel column PD-10 (produced by Pharmacia), while the buffer was replaced with phosphate buffer saline.

Thus 3.0 mg of galactose-modified rIFN-αA was obtained, the number of galactose molecules bound to each interferon molecule being 10. Protein contents and modifying galactose contents were determined by the PIERCE BCA method (BCA protein assay reagent, produced by PIERCE Company) and amino acid analysis, respectively.

Example 2

100 mg of cyanomethyl 2,3,4,6-tetra-o-acetyl-1-thio-β-D-galactopyranoside was dissolved in 2.5 ml of methanol. To this solution was added 4.9 μl of sodium methoxide (28% in methanol solution, produced by Wako Pure Chemical Industries), followed by a reaction at room temperature for 72 hours with stirring. A 450 μl portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of rIFN-αA, at 6.25 mg/ml, pH 6.5 (0.1M phosphate buffer). After a reaction at room temperature for 30 hours, 100 μl of a 1M aqueous acetic acid solution was added to terminate the reaction. The unreacted galactopyranoside was removed using a gel column PD-10 (produced by Pharmacia), while the buffer was replaced with a 25 mM ammonium acetate buffer containing 0.13M NaCl, pH 5.5.

Thus 4.8 mg of galactose-modified rIFN-αA was obtained, the number of galactose molecules bound to each interferon molecule being 3.3. Protein contents and modifying galactose contents were determined by the PIERCE BCA method (BCA protein assay reagent, produced by PIERCE Company) and the sulfuric acid-phenol method, respectively.

Example 3

100 mg of cyanomethyl 2,3,4,6-tetra-o-acetyl-1-thio-β-D-galactopyranoside was dissolved in 2.5 ml of methanol. To this solution was added 4.9 μl of sodium methoxide (28% in methanol solution, produced by Wako Pure Chemical Industries), followed by a reaction at room temperature for 72 hours with stirring. A 450 μl portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of rIFN-αA, at 6.25 mg/ml, pH 7.0 (0.1M phosphate buffer). After a reaction at room temperature for 30 hours, 100 μl of a 1M aqueous acetic acid solution was added to terminate the reaction. The unreacted galactopyranoside was removed using a gel column PD-10, while the buffer was replaced with a 25 mM ammonium acetate buffer containing 0.13M NaCl, pH 5.5.

Thus 5.2 mg of galactose-modified rIFN-αA was obtained, the number of galactose molecules bound to each interferon molecule being 3.8. Protein contents and modifying galactose contents were determined by the PIERCE BCA method (BCA protein assay reagent, produced by PIERCE Company) and the sulfuric acid-phenol method, respectively.

Example 4

100 mg of cyanomethyl 2,3,4,6-tetra-o-acetyl-1-thio-β-D-galactopyranoside was dissolved in 2.5 ml of methanol. To this solution was added 4.9 μl of sodium methoxide (28% in methanol solution, produced by Wako Pure Chemical Industries), followed by a reaction at room temperature for 72 hours with stirring. A 450 μl portion of this methanol solution was dispensed to a test tube, and the methanol was thoroughly evaporated using a nitrogen stream. To the resulting dry reaction product 2-imino-2-methoxyethyl-1-thio-β-D-galactopyranoside, 1 ml of rIFN-αA, at 6.25 mg/ml, pH 7.5 (0.1M phosphate buffer). After reaction at room temperature for 30 hours, 100 μl of a 1M aqueous acetic acid solution was added to terminate the reaction. The unreacted galactopyranoside was removed using a gel column PD-10, while the buffer was replaced with a 25 mM ammonium acetate buffer containing 0.13M NaCl, pH 5.5.

Thus 5.6 mg of galactose-modified rIFN-αA was obtained, the number of galactose molecules bound to each interferon molecule being 5.3. Protein contents and modifying galactose contents were determined by the PIERCE BCA method (BCA protein assay reagent, produced by PIERCE Company) and the sulfuric acid-phenol method, respectively.

Example 5

100 mg of cyanomethyl 2,3,4,6-tetra-o-acetyl-1-thio-β-D-galactopyranoside was dissolved in 2.5 ml of methanol. To this solution was added 4.9 μl of sodium methoxide (28% in methanol solution, produced by Wako Pure Chemical Industries), followed by a reaction at room temperature for 72 hours with stirring. A 450 μl portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of rIFN-αA, at 6.25 mg/ml, pH 8.1 (0.1M phosphate buffer). After a reaction at room temperature for 30 hours, 100 μl of a 1M aqueous acetic acid solution was added to terminate the reaction. The unreacted galactopyranoside was removed using a gel column PD-10, while the buffer was replaced with a 25 mM ammonium acetate buffer containing 0.13M NaCl, pH 5.5.

Thus 5.8 mg of galactose-modified rIFN-αA was obtained, the number of galactose molecules bound to each interferon molecule being 5.8. Protein contents and modifying galactose contents were determined by the PIERCE BCA method (BCA protein assay reagent, produced by PIERCE Company) and the sulfuric acid-phenol method, respectively.

Example 6

100 mg of cyanomethyl 2,3,4,6-tetra-o-acetyl-1-thio-β-D-galactopyranoside was dissolved in 2.5 ml of methanol. To this solution was added 4.9 μl of sodium methoxide (28% in methanol solution, produced by Wako Pure Chemical Industries), followed by a reaction at room temperature for 72 hours with stirring. A 450 μl portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of rIFN-αA, at 6.25 mg/ml, pH 8.7 (0.1M phosphate buffer). After a reaction at room temperature for 30 hours, 100 μl of a 1M aqueous acetic acid solution was added to terminate the reaction. The unreacted galactopyranoside was removed using a gel column PD-10, while the buffer was replaced with a 25 mM ammonium acetate buffer containing 0.13M NaCl, pH 5.5.

Thus 5.0 mg of galactose-modified rIFN-αA was obtained, the number of galactose molecules bound to each interferon molecule being 6.8. Protein contents and modifying galactose contents were determined by the PIERCE BCA method (BCA protein assay reagent, produced by PIERCE Company) and the sulfuric acid-phenol method, respectively.

Example 7

1.0 g of cyanomethyl 2,3,4,6-tetra-o-acetyl-1-thio-β-D-galactopyranoside was dissolved in 25 ml of methanol. To this solution was added 50 μl of sodium methoxide (28% in methanol solution, produced by Wako Pure Chemical Industries), followed by a reaction at room temperature for 72 hours with stirring. A 4.0 ml portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of rIFN-αA, at 6.25 mg/ml, pH 6.5 (0.1M phosphate buffer). After reaction at room temperature for 24 hours, 100 μl of a 1 M aqueous acetic acid solution was added to terminate the reaction. The unreacted galactopyranoside was removed using a gel column PD-10, while the buffer was replaced with a 25 mM ammonium acetate buffer containing 0.13M NaCl, pH 5.5.

Thus 6.4 mg of galactose-modified rIFN-αA was obtained, the number of galactose molecules bound to each interferon molecule being 9.5. Protein contents and modifying galactose contents were determined by the PIERCE BCA method (BCA protein assay reagent, produced by PIERCE Company) and the sulfuric acid-phenol method, respectively.

Example 8

1.0 g of cyanomethyl 2,3,4,6-tetra-o-acetyl-1-thio-β-D-galactopyranoside was dissolved in 25 ml of methanol. To this solution was added 50 μl of sodium methoxide (28% in methanol solution, produced by Wako Pure Chemical Industries), followed by a reaction at room temperature for 72 hours with stirring. A 4.0 ml portion of this methanol solution was dispensed to a test tube, and the methanol was thoroughly evaporated using a nitrogen stream. To the resulting dry reaction product 2-imino- 2-methoxyethyl-1-thio-β-D-galactopyranoside was added 1 ml of rIFN-αA, at 6.25 mg/ml, pH 7.0 (0.1M phosphate buffer). After a reaction at room temperature for 24 hours, 100 μl of a 1M aqueous acetic acid solution was added to terminate the reaction. The unreacted galactopyranoside was removed using a gel column PD-10, while the buffer was replaced with a 25 mM ammonium acetate buffer containing 0.13M NaCl, pH 5.5.

Thus 6.3 mg of galactose-modified rIFN-αA was obtained, the number of galactose molecules bound to each interferon molecule being 8.5. Protein contents and modifying galactose contents were determined by the PIERCE BCA method (BCA protein assay reagent, produced by PIERCE Company) and the sulfuric acid-phenol method, respectively.

Example 9

1.0 g of cyanomethyl 2,3,4,6-tetra-o-acetyl-1-thio-β-D-galactopyranoside was dissolved in 25 ml of methanol. To this solution was added 50 μl of sodium methoxide (28% in methanol solution, produced by Wako Pure Chemical Industries), followed by a reaction at room temperature for 72 hours with stirring. A 4.0 ml portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of rIFN-αA, at 6.25 mg/ml, pH 7.5 (0.1M phosphate buffer). After a reaction at room temperature for 24 hours, 100 μl of a 1M aqueous acetic acid solution was added to terminate the reaction. The unreacted galactopyranoside was removed using a gel column PD-10, while the buffer was replaced with a 25 mM ammonium acetate buffer containing 0.13M NaCl, pH 5.5.

Thus 5.9 mg of galactose-modified rIFN-αA was obtained, the number of galactose molecules bound to each interferon molecule being 9.7. Protein contents and modifying galactose contents were determined by the PIERCE BCA method (BCA protein assay reagent, produced by PIERCE Company) and the sulfuric acid-phenol method, respectively.

Example 10

1.0 g of cyanomethyl 2,3,4,6-tetra-o-acetyl-1-thio-β-D-galactopyranoside was dissolved in 25 ml of methanol. To this solution was added 50 μl of sodium methoxide (28% in methanol solution, produced by Wako Pure Chemical Industries), followed by a reaction at room temperature for 72 hours with stirring. A 4.0 ml portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of rIFN-αA, at 6.25 mg/ml, pH 8.1 (0.1M phosphate buffer). After reaction at room temperature for 24 hours, 100 μl of a 1M aqueous acetic acid solution was added to terminate the reaction. The unreacted galactopyranoside was removed using a gel column PD-10, while the buffer was replaced with a 25 mM ammonium acetate buffer containing 0.13M NaCl, pH 5.5.

Thus 5.7 mg of galactose-modified rIFN-αA was obtained, the number of galactose molecules bound to each interferon molecule being 8.8. Protein contents and modifying galactose contents were determined by the PIERCE BCA method (BCA protein assay reagent, produced by PIERCE Company) and the sulfuric acid-phenol method, respectively.

Example 11

1.0 g of cyanomethyl 2,3,4,6-tetra-o-acetyl-1-thio-β-D-galactopyranoside was dissolved in 25 ml of methanol. To this solution was added 50 μl of sodium methoxide (28% in methanol solution, produced by Wako Pure Chemical Industries), followed by a reaction at room temperature for 72 hours with stirring. A 4.0 ml portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of rIFN-αA, at 6.25 mg/ml, pH 8.7 (0.1M phosphate buffer). After a reaction at room temperature for 24 hours, 100 μl of a 1M aqueous acetic acid solution was added to terminate the reaction. The unreacted galactopyranoside was removed using a gel column PD-10, while the buffer was replaced with a 25 mM ammonium acetate buffer containing 0.13M NaCl, pH 5.5.

Thus 5.1 mg of galactose-modified rIFN-αA was obtained, the number of galactose molecules bound to each interferon molecule being 11. Protein contents and modifying galactose contents were determined by the PIERCE BCA method (BCA protein assay reagent, produced by PIERCE Company) and the sulfuric acid-phenol method, respectively.

Example 12

1.0 g of cyanomethyl 2,3,4,6-tetra-o-acetyl-1-thio-β-D-galactopyranoside was dissolved in 25 ml of methanol. To this solution was added 50 μl of sodium methoxide (28% in methanol solution, produced by Wako Pure Chemical Industries), followed by a reaction at room temperature for 72 hours with stirring. A 40 μl portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of rIFN-αA, at 6.25 mg/ml, pH 6.5 (0.1M phosphate buffer). After a reaction at room temperature for 24 hours, 100 μl of a 1M aqueous acetic acid solution was added to terminate the reaction. The unreacted galactopyranoside was removed using a gel column PD-10, while the buffer was replaced with a 25 mM ammonium acetate buffer containing 0.13M NaCl, pH 5.5.

Thus 4.7 mg of galactose-modified rIFN-αA was obtained, the number of galactose molecules bound to each interferon molecule being 0.6. Protein contents and modifying galactose contents were determined by the PIERCE BCA method (BCA protein assay reagent, produced by PIERCE Company) and the sulfuric acid-phenol method, respectively.

Example 13

1.0 g of cyanomethyl 2,3,4,6-tetra-o-acetyl-1-thio-β-D-galactopyranoside was dissolved in 25 ml of methanol. To this solution was added 50 μl of sodium methoxide (28% in methanol solution, produced by Wako Pure Chemical Industries), followed by a reaction at room temperature for 72 hours with stirring. A 40 μl portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of rIFN-αA, at 6.25 mg/ml, pH 7.0 (0.1M phosphate buffer). After a reaction at room temperature for 24 hours, 100 μl of a 1M aqueous acetic acid solution was added to terminate the reaction. The unreacted galactopyranoside was removed using a gel column PD-10, while the buffer was replaced with a 25 mM ammonium acetate buffer containing 0.13M NaCl, pH 5.5.

Thus 5.1 mg of galactose-modified rIFN-αA was obtained, the number of galactose molecules bound to each interferon molecule being 0.6. Protein contents and modifying galactose contents were determined by the PIERCE BCA method (BCA protein assay reagent, produced by PIERCE Company) and the sulfuric acid-phenol method, respectively.

Example 14

1.0 g of cyanomethyl 2,3,4,6-tetra-o-acetyl-1-thio-β-D-galactopyranoside was dissolved in 25 ml of methanol. To this solution was added 50 μl of sodium methoxide (28% in methanol solution, produced by Wako Pure Chemical Industries), followed by a reaction at room temperature for 72 hours with stirring. A 40 μl portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of rIFN-αA, at 6.25 mg/ml, pH 7.5 (0.1M phosphate buffer). After a reaction at room temperature for 24 hours, 100 μl of a 1M aqueous acetic acid solution was added to terminate the reaction. The unreacted galactopyranoside was removed using a gel column PD-10, while the buffer was replaced with a 25 mM ammonium acetate buffer containing 0.13M NaCl, pH 5.5.

Thus 5.0 mg of galactose-modified rIFN-αA was obtained, the number of galactose molecules bound to each interferon molecule being 1.1. Protein contents and modifying galactose contents were determined by the PIERCE BCA method (BCA protein assay reagent, produced by PIERCE Company) and the sulfuric acid-phenol method, respectively.

Example 15

1.0 g of cyanomethyl 2,3,4,6-tetra-o-acetyl-1-thio-β-D-galactopyranoside was dissolved in 25 ml of methanol. To this solution was added 50 μl of sodium methoxide (28% in methanol solution, produced by Wako Pure Chemical Industries), followed by a reaction at room temperature for 72 hours with stirring. A 40 μl portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of rIFN-αA, at 6.25 mg/ml, pH 8.1 (0.1M phosphate buffer). After a reaction at room temperature for 24 hours, 100 μl of a 1M aqueous acetic acid solution was added to terminate the reaction. The unreacted galactopyranoside was removed using a gel column PD-10, while the buffer was replaced with a 25 mM ammonium acetate buffer containing 0.13M NaCl, pH 5.5.

Thus 5.1 mg of galactose-modified rIFN-αA was obtained, the number of galactose molecules bound to each interferon molecule being 1.6. Protein contents and modifying galactose contents were determined by the PIERCE BCA method (BCA protein assay reagent, produced by PIERCE Company) and the sulfuric acid-phenol method, respectively.

Example 16

1.0 g of cyanomethyl 2,3,4,6-tetra-o-acetyl-1-thio-β-D-galactopyranoside was dissolved in 25 ml of methanol. To this solution was added 50 μl of sodium methoxide (28% in methanol solution, produced by Wako Pure Chemical Industries), followed by a reaction at room temperature for 72 hours with stirring. A 40 μl portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of rIFN-αA, at 6.25 mg/ml, pH 8.7 (0.1M phosphate buffer). After a reaction at room temperature for 24 hours, 100 μl of a 1M aqueous acetic acid solution was added to terminate the reaction. The unreacted galactopyranoside was removed using a gel column PD-10, while the buffer was replaced with a 25 mM ammonium acetate buffer containing 0.13M NaCl, pH 5.5.

Thus 4.6 mg of galactose-modified rIFN-αA was obtained, the number of galactose molecules bound to each interferon molecule being 2.0. Protein contents and modifying galactose contents were determined by the PIERCE BCA method (BCA protein assay reagent, produced by PIERCE Company) and the sulfuric acid-phenol method, respectively.

Experimental Example 1: Changes over Time in Serum Levels after Intravenous Administration Changes over time in serum levels of the galactose-modified interferon-αAs obtained in Examples 1, 3 and 16 were monitored after intravenous administration to rats. Determinations were made by enzyme immunoassay. For control, non-modified interferon-αA was intravenously administered. The results are shown in FIG. 1.

From FIG. 1, it is seen that the non-modified interferon-αA hardly disappears from the serum within 10 minutes, while the galactose-modified interferon-αAs disappear rapidly.

Experimental Example 2: Hepatic Migration Testing by Liver Perfusion Experiment

The hepatic migration of the galactose-modified interferon-αA obtained in Example 1 was determined by the rat liver perfusion method. Cannulation was performed on the rat hepatic portal vein and cava. While perfusing the galactose-modified interferon-αA from the portal side (Cin), perfusate on the cava side (Cout) was collected periodically to monitor changes over time in the concentration ratio of Cin and Cout. In this experiment, the inferior cava was ligated with surgical suture. For control, the ratio of Cin and Cout in non-modified interferon-αA was determined. The results are shown in FIG. 2.

Figure 2:
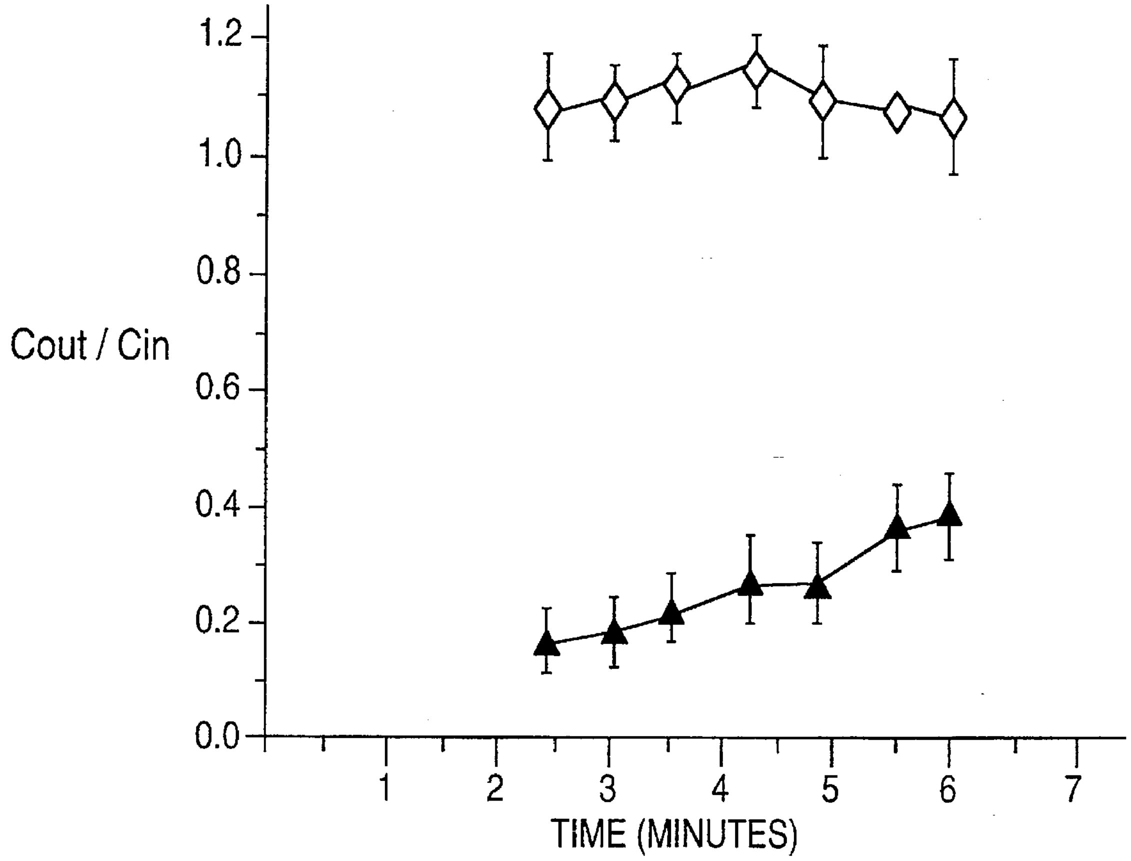
FIG. 2 shows the results of an experiment in which the hepatic migration of non-modified and galactose-modified interferon-αA was determined by the rat liver perfusion method. ◇ and ▲ show a non-modified interferon-αA and the galactose-modified interferon-αA obtained in Example 1, respectively.

From FIG. 2, it is seen that the non-modified interferon-αA had a Cout/Cin ratio of nearly 1, demonstrating the absence of hepatic migration, while the galactose-modified interferon-αA had a Cout/Cin ratio of 0.1 to 0.4, demonstrating hepatic migration.

Experimental Example 3: Determination of 2–5AS Activity Using Cultured Hepatocytes The increase in 2–5AS activity in cultured rat hepatocytes by galactose-modified interferon-αA was examined. Rat hepatocytes were collected via collagenase treatment. The thus-obtained $1\times10^2$ hepatocytes were dispersed in 1 ml of an Eagle MEM (Eagle minimum essential medium) containing 10% FCS (fetal calf serum), and the galactose-modified interferon-αA of Example 1 or non-modified interferon-αA was added to various concentrations. After 1 day of cultivation in an incubator at 37° C., cells were separated by centrifugation and added to 0.01% Triton X-100 (produced by Wako Pure Chemical Industries) and homogenized. After cell debris was removed through a 0.2 μm filter, the filtrate was assayed for 2–5AS activity, using a 2–5A assay kit (Eiken Chemical Co., Ltd.). The results are shown in FIG. 3.

Figure 3:
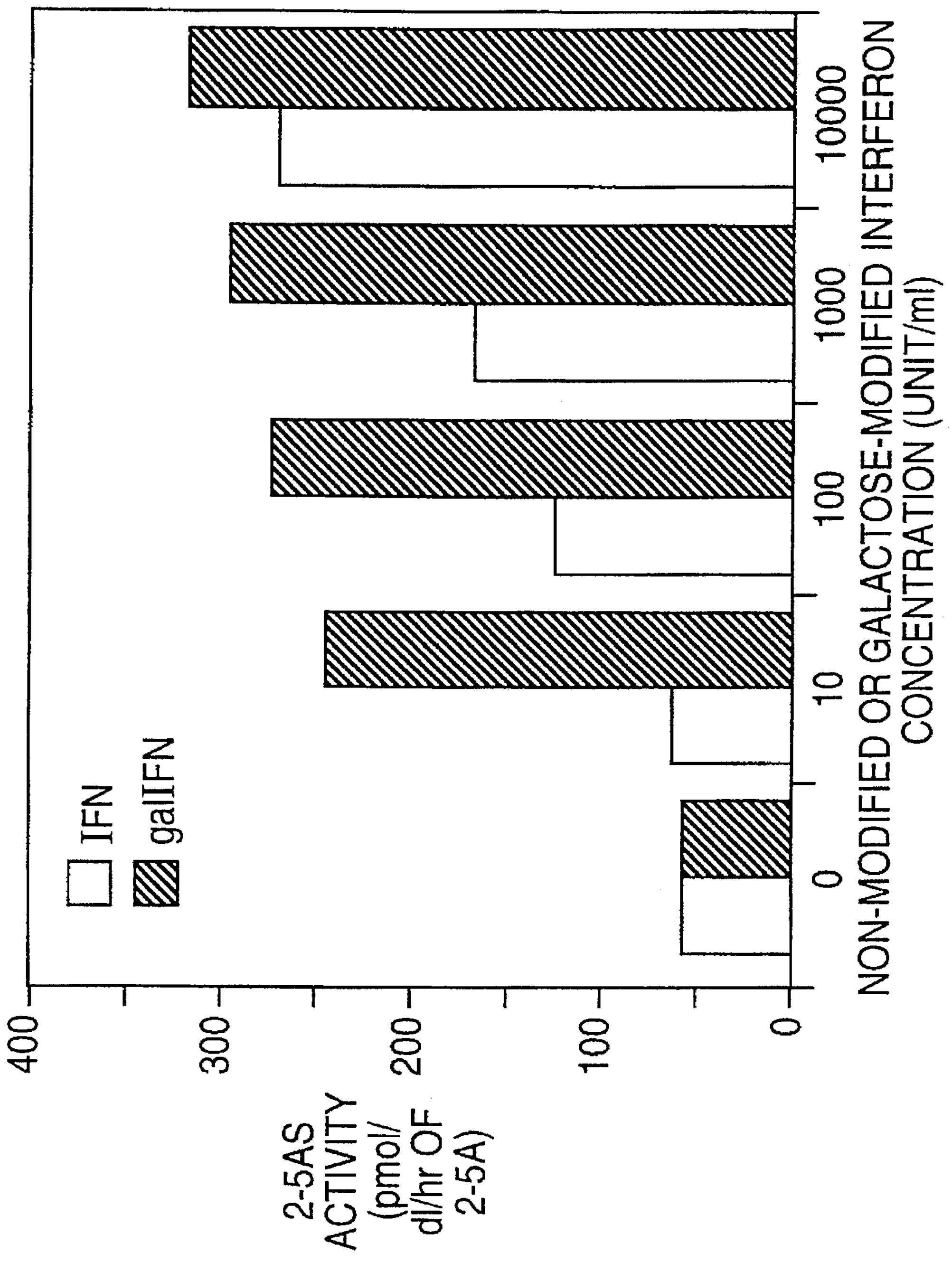
FIG. 3 shows the results of a determination of 2',5'-oligoadenylate synthetase (2–5AS) activity following non-modified or galactose-modified interferon-αA administration to primary culture of rat hepatocytes. IFN and galIFN show a non-modified interferon-αA and the galactose-modified interferon-αA obtained in Example 1, respectively.

From FIG. 3, it is seen that the galactose-modified interferon-αA raised the 2–5AS activity at concentrations 1/100 to 1/1000 as low as those of the non-modified interferon-αA. This finding demonstrates that as a result of marked improvement in galactose-modified interferon-αA migration to hepatocytes, interferon-αA activity in hepatocytes is increased. For this reason, the galactose-modified interferon-αA results in an increased 2–5AS activity at lower concentrations than with the non-modified interferon-αA.

Experimental Example 4: In Vitro Determination of Antiviral Activity

An experiment was conducted in accordance with a known method [M. Rubinstein et al.: Proc. Natl. Acad. Sci. USA, 76, 640 (1979); R. K. Maheshwari and R. M. Friedman: Virol. 101, 399 (1980)]. Specifically, interferon or galactose-modified interferon was diluted to various concentrations with a medium containing 10% fetal calf serum (Eagle's MEM) and added to a 96-well microplate at 50 μl per well. Subsequently, MDBK cells ($4\times10^5$ cells/ml), suspended in the same medium, were added at 50 μl per well, followed by incubation at 37° C. for 3 hours. A viral (VSV) preparation ($2\times10^5$ PFU or plaque forming unit/ml), diluted with the same medium, was further added at 50 μl per well, followed by cultivation at 37° C. for 40 hours.

After staining with a 0.1% Neutral Red solution (25 μl/well), the cells were cultured at 37° C. for 1 more hour, after which a 4% formalin solution (25 μl/well) was added to inactivate the virus and fix the cells. After the plate was kept standing for 30 minutes, it was irradiated with UV, washed with water and dried. The dye was then extracted with a 1:1 ethylene glycol-ethanol mixture (100 μl/well) containing 2% (w/v) citric acid, the absorbance at 540 nm being determined.

Figure 4:
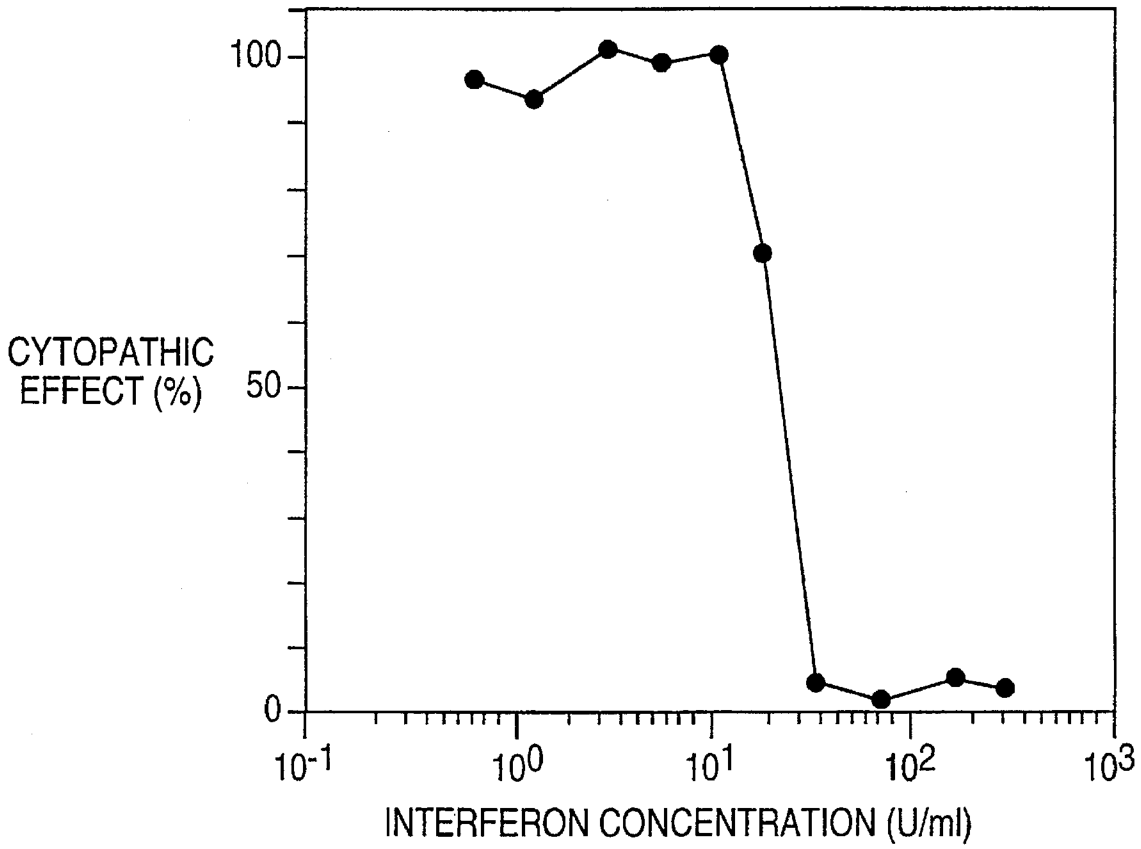
FIG. 4 shows the standard curve for IFN-αA obtained in the in vitro antiviral activity test described in Experimental Example 4.

The standard working curve for the antiviral activity of the standard preparation of IFN-αA is shown in FIG. 4.

Example 17: Synthesis (1) of Galactose-modified IFN-αA 100 mg of cyanomethyl 2,3,4,6-tetra-o-acetyl-1-thio-β-D-galactopyranoside, the cyanomethyl thioglycoside of galactose, was dissolved in 2.5 ml of methanol. To this solution was added 4.9 μl of a 28% $NaOCH_3$ methanol solution, followed by a reaction at room temperature for 72 hours. A 200 to 450 μl portion of the reaction broth was dispensed to a test tube, and the methanol was evaporated in a nitrogen stream. To the thus obtained 2-imino-2-methoxyethyl-1-thio-β-D-galactopyranoside was added 1.0 ml of a 0.1M phosphate buffer (pH 7.0, 6.25 mg/ml) containing IFN-αA, followed by a reaction at room temperature for 30 hours. After the reaction was terminated by addition of a 1 M acetic acid solution, the reaction product was purified by PD-10 column chromatography using 25 mM ammonium acetate-0.13M NaCl (pH 5.5) as eluent. About 4.8 to 5.8 mg of galactose-modified IFN-αA was obtained.

Protein concentrations were determined, using a commercially available BCA protein assay kit (PIERCE Co.). The number of galactose molecules bound per IFN molecule was determined by amino acid analysis. Antiviral activity was determined as directed in Experimental Example 4.

The results are given in Table 1. The interferon bound with 4.1 galactose molecules possessed antiviral activity equivalent to that of the non-modified interferon, while the interferon bound with 5.7 galactose molecules possessed a decreased activity of 63%.

TABLE 1

| Number of Modifying Galactose Molecules | Protein Concentration (mg/ml) | Antiviral Activity (× $10^8$ U/ml) | Specific Activity (× $10^8$ U/mg, %) | |
|---|---|---|---|---|
| 0 | 1.00 | 2.1 | 2.1 | 100 |
| 3.0 | 2.04 | 3.3 | 1.6 | 78 |
| 4.1 | 2.18 | 4.6 | 2.1 | 101 |
| 5.7 | 2.09 | 2.7 | 1.3 | 63 |

U: Activity unit

Example 18: Synthesis (2) of Galactose-modified IFN-αA

To 2-imino-2-methoxyethyl-1-thio-β-D-galactopyranoside prepared in the same manner as in Example 17 (in an amount equivalent to 150 to 190 μl reaction broth) was added 1.0 ml of a 0.1M phosphate buffer (pH 7.0, 1.82 mg/ml) containing IFN-αA, followed by a reaction at room temperature for 30 hours. Then the same treatment as in Example 17 was conducted to yield purified galactose-modified IFN-αA.

The results are given in Table 2. Under any set of reaction conditions, yield was 90 to 97%, and the number of modifying galactose molecules increased, depending on the amount of activated galactose added.

TABLE 2

| Amount of Activated Galactose Added (μl) | Number of Modifying Galactose Molecules | Yield (%) |
|---|---|---|
| 150 | 2.8 | 95 |
| 170 | 2.9 | 97 |
| 190 | 3.1 | 90 |

Example 19: Synthesis (3) of Galactose-modified IFN-αA

To 2-imino-2-methoxyethyl-1-thio-β-galactopyranoside prepared in the same manner as in Example 17 (in an amount equivalent to 25 to 400 μl reaction broth) was added 1.0 ml of a 0.1M phosphate buffer (pH 8.0, 0.54 mg/ml) containing IFN-αA, followed by a reaction at room temperature for 30 hours. Then the same treatment as in Example 17 was conducted to yield purified galactose-modified IFNαA.

The results are given in Table 3. The number of modifying galactose molecules increased, depending on the amount of activated galactose added. Also, when the number of modifying galactose molecules was not more than 5, over 80% antiviral activity was retained.

TABLE 3

| Amount of Activated Galactose Added (μl) | Number of Modifying Galactose Molecules | Antiviral Activity (%) |
|---|---|---|
| 0 | 0 | 100 |
| 25 | 1.3 | 141 |
| 50 | 2.4 | 143 |
| 100 | 4.6 | 86 |
| 200 | 7.7 | 65 |
| 400 | 9.6 | 51 |

Example 20: Synthesis (4) of Galactosylated IFN-αA

To 9.7 mg of IFN-αA dissolved in 1.0 ml of 0.2M sodium borate buffer (pH 8.0) were added 10 mg of lactose and 10 mg of sodium cyanoborohydride, followed by incubation at 37° C. for 5 days. After the reaction was terminated by addition of 0.1 ml of a 1M acetic acid solution, the reaction product was purified by gel filtration chromatography using a PD-10 column equilibrated with 25 mM ammonium acetate-0.13M NaCl solution.

1.6 mg of IFN-αA modified with 4.7 galactose molecules was obtained. The antiviral activity was about 81% of that of the non-modified interferon-αA.

Experimental Example 5: Hepatic Orientation of Galactose-modified IFN-αA (1)

Each of non-modified interferon-ah and the IFN-αA bound with 4.1 galactose molecules prepared in Example 17 was given to three rats by intramuscular administration ($4\times10^6$ U/animal). One hour later the animals were exsanguinated, the liver, kidney and serum IFN-αA concentrations were determined by a known method of enzyme immunoassay (ELISA).

The results are given in Table 4. The galactose-modified IFN-αA showed increased hepatic migration, with a hepatic selectivity about 80 times that of the non-modified IFN-αA. The two IFN-αAs were almost equivalent to each other in renal migration in terms of serum levels.

TABLE 4

| | Concentration (U/ml or U/g) | |
|---|---|---|
| Tissue | Non-modified IFN-αA | Galactose-modified IFN-αA |
| Serum | 5490 ± 252 (1.00) | 905 ± 131 (1.00) |
| Liver | 164 ± 15 (0.03) | 2141 ± 719 (2.37) |
| Kidney | 32471 ± 3195 (5.91) | 4775 ± 841 (5.28) |

Figures for concentration are shown in mean ± SD. Figures in parentheses are concentration ratios.

Experimental Example 6: Hepatic Orientation of Galactose-modified IFN-αA (2)

Each of phosphate buffer saline (PBS), non-modified interferon-αA and the IFN-αA bound with 4.1 galactose molecules prepared in Example 17 was intramuscularly administered to rats ($4\times10^6$ U/animal). Three and 24 hours later livers were excised. The liver was homogenized in 4 ml of a 0.1M sodium acetate buffer (pH 5.0), followed by centrifugation. The IFN-αA concentration in the supernatant was determined by the ELISA described in Experimental Example 5 and the antiviral activity test described in Experimental Example 4.

The results are given in Table 5. The galactose-modified IFN-αA showed better hepatic accumulation and retention than the non-modified IFN-αA, significant antiviral activity being noted in the liver even 24 hours after administration.

TABLE 5

| | ELISA Activity (U/ml) | | Antiviral Activity (U/ml) | |
|---|---|---|---|---|
| Subject drug | 3 Hours | 24 Hours | 3 Hours | 24 Hours |
| PBS | <3 | <3 | <50 | <50 |
| Non-modified interferon-αA | 37 | <3 | <50 | <50 |
| Galactose-modified IFN-αA | 74 | <3 | 136 | 92 |

Example 21

100 mg of cyanomethyl 2,3,4,6-tetra-o-acetyl-1-thio-β-D-galactopyranoside, the cyanomethyl thioglycoside of galactose, was dissolved in 2.5 ml of methanol. To this solution was added 49 μl of sodium methoxide (28% in methanol solution, produced by Wako Pure Chemical Industries), followed by a reaction at 25° C. for 72 hours. A 30 μl portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of recombinant interleukin-2 (rIL-2), at 0.7 mg/ml, pH 8.5 (0.1M phosphate buffer). After a reaction at 25° C. for 24 hours, 100 μl of a 1 M aqueous acetic acid solution was added to terminate the reaction. The unreacted galactopyranoside was removed using a gel column PD-10 (produced by Pharmacia), while the buffer was replaced with a 25 mM ammonium acetate buffer containing 0.13M NaCl, pH 5.5. Thus 473 μg of galactose-modified rIL-2 was obtained, the number of galactose molecules bound to each rIL-2 molecule being 3.4 as determined by amino acid analysis.

Example 22

100 mg of cyanomethyl 2,3,4,6-tetra-o-acetyl-1-thio-β-D-galactopyranoside, the cyanomethyl thioglycoside of galactose, was dissolved in 2.5 ml of methanol. To this solution was added 49 μl of sodium methoxide (28% in methanol solution, produced by Wako Pure Chemical Industries), followed by a reaction at 25° C. for 72 hours. A 40 μl portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of rIL-2, at 0.7 mg/ml, pH 8.5 (0.1M phosphate buffer). After a reaction at 25° C. for 24 hours, 100 μl of a 1 M aqueous acetic acid solution was added to terminate the reaction. The unreacted galactopyranoside was removed using a gel column PD-10 (produced by Pharmacia), while the buffer was replaced with a 25 mM ammonium acetate buffer containing 0.13M NaCl, pH 5.5. Thus 493 μg of galactose-modified rIL-2 was obtained, the number of galactose molecules bound to each rIL-2 molecule being 4.3 as determined by amino acid analysis.

Example 23

100 mg of cyanomethyl 2,3,4,6-tetra-o-acetyl-1-thio-β-D-galactopyranoside, the cyanomethyl thioglycoside of galactose, was dissolved in 2.5 ml of methanol. To this solution was added 49 μl of sodium methoxide (28% in methanol solution, produced by Wako Pure Chemical Industries), followed by a reaction at 25° C. for 72 hours with stirring. A 50 μl portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 1 ml of rIL-2, at 0.7 mg/ml, pH 8.5 (0.1M phosphate buffer). After a reaction at 25° C. for 24 hours, 100 μl of a 1M aqueous acetic acid solution was added to terminate the reaction. The unreacted galactopyranoside was removed using a gel column PD-10 (produced by Pharmacia), while the buffer was replaced with a 25 mM ammonium acetate buffer containing 0.13M NaCl, pH 5.5. Thus 533 μg of galactose-modified rIL-2 was obtained, the number of galactose molecules bound to each rIL-2 molecule being 5.2 as determined by amino acid analysis.

Experimental Example 7

Table 6 shows the results of determination of the residual specific bioactivities of the galactose-bound rIL-2 species obtained in Examples 21, 22 and 23. Bioactivity was determined by the method of Tada et al. [J. Immunol. Methods 93, 157–165 (1986)], using the IL-2-dependent mouse natural killer cell line NKC3.

TABLE 6

| Number of Modifying Galactose Molecules and Residual Bioactivity | |
|---|---|
| Number of Modifying Galactose Molecules | Residual Specific Activity (%) |
| 3.4 | 94 |
| 4.3 | 88 |
| 5.2 | 82 |

Example 24

To 1.5 ml of a 0.7 mg/ml interferon-αA solution, pH 9.5 (0.1M sodium carbonate), 0.15 ml of β-D-galactopyranosylphenylisothiocyanate (produced by SIGMA), 0.5 mg/ml, pH 9.5 (0.1M sodium carbonate), was added, followed by a reaction at 25° C. for 24 hours. The unreacted β-D-galactopyranosyl-phenylisothiocyanate was removed using a gel column PD-10 (produced by Pharmacia), while the buffer was replaced with a 25 mM ammonium acetate buffer containing 0.13M NaCl, pH 5.5. Thus 798 μg of galactose-modified interferon-αA was obtained, the number of galactose molecules bound to each interferon-αA molecule being 2.0 as determined by amino acid analysis.

Example 25

To 1.5 ml of a 0.7 mg/ml interferon-αA solution, pH 9.5 (0.1M sodium carbonate), 0.5 ml of β-D-galactopyranosylphenylisothiocyanate (produced by SIGMA), 0.5 mg/ml, pH 9.5 (0.1M sodium carbonate), was added, followed by a reaction at 25° C. for 24 hours. The unreacted β-D-galactopyranosyl-phenylisothiocyanate was removed using a gel column PD-10 (produced by Pharmacia), while the buffer was replaced with a 25 mM ammonium acetate buffer containing 0.13M NaCl, pH 5.5. Thus 860 μg of galactose-modified interferon-αA was obtained, the number of galactose molecules bound to each interferon-αA molecule being 4.0 as determined by amino acid analysis.

Example 26

To 1.5 ml of a 0.7 mg/ml interferon-αA solution, pH 9.5 (0.1M sodium carbonate), 0.75 ml of β-D- galactopyranosylphenylisothiocyanate (produced by SIGMA), 0.5 mg/ml, pH 9.5 (0.1M sodium carbonate), was added, followed by a reaction at 25° C. for 24 hours. The unreacted β-D-galactopyranosyl-phenylisothiocyanate was removed using a gel column PD-10 (produced by Pharmacia), while the buffer was replaced with a 25 mM ammonium acetate buffer containing 0.13M NaCl, pH 5.5. Thus 870 μg of galactose-modified interferon-αA was obtained, the number of galactose molecules bound to each interferon-αA molecule being 4.8 as determined by amino acid analysis.

Example 27: Synthesis of galactose-modified mouse IFN-β

100 mg of cyanomethyl 2,3,4,6-tetra-o-acethyl-1-thio-β-D-galactopyranoside, the cyanomethyl thioglycoside of galactose, was dissolved in 2.5 ml of methanol. To this solution was added 4.9 μl of sodium methoxide (28% in methanol solution, produced by Wako Pure Chemical Industries), followed by a reaction at 25° C. for 72 hours. A 360 μl portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 120 μl of 0.1M phosphate buffer (pH 7.0) to dissolve the product. Then, to the buffer was gradually added recombinant mouse interferon-β (200 μg/1.2 ml: purchased from Funakoshi Company) dissolved in 0.1M phosphate buffer (pH 7.0). After a reaction at 25° C. for 24 hours, the unreacted galactopyranoside was removed using a gel column PD-10 (produced by Pharmacia), while the buffer was replaced with a 50 mM ammonium acetate buffer (pH 4.5).

Thus, 208 μg of galactose-modified IFN-β was obtained, the number of galactose molecules bound to each IFN-β molecule being 2.5 as determined by amino acid analysis.

Example 28

100 mg of cyanomethyl 2,3,4,6-tetra-o-acethyl-1-thio-β-D-galactopyranoside, the cyanomethyl thioglycoside of galactose, was dissolved in 2.5 ml of methanol. To this solution was added 4.9 μl of sodium methoxide (28% in methanol solution, produced by Wako Pure Chemical Industries), followed by a reaction at 25° C. for 72 hours. A 420 μl portion of this methanol solution was dispensed to a test tube, and the methanol was thoroughly evaporated using a nitrogen stream. To the resulting dry reaction product 2-imino-2-methoxyethyl-1-thio-β-D-galactopyranoside was added 120 μl of 0.1M phosphate buffer (pH 7.0) to dissolve the product. Then, to the buffer was gradually added recombinant mouse interferon-β (200 μg/1.2 ml: purchased from Funakoshi Company) dissolved in 0.1M phosphate buffer (pH 7.0). After a reaction at 25° C. for 24 hours, the unreacted galactopyranoside was removed using a gel column PD-10 (produced by Pharmacia), while the buffer was replaced with a 50 mM ammonium acetate buffer (pH 4.5).

Thus, 212 μg of galactose-modified IFN-β was obtained, the number of galactose molecules bound to each IFN-β molecule being 4.0 as determined by amino acid analysis.

Experimental Example 8: 2–5AS Activity in Liver of Mice Injected Mouse Interferon-β (IFN-β)

Each of non-modified mouse IFN-β and the IFN-β bound with 4.0 galactose molecules prepared in Example 28 was intraperitoneally given to mice once or twice at the dose of 0.2 or 1.0 μg/day/mouse as IFN-β. Each group consisted of four C3H mice. One day later the animals were exsanguinated and the liver was homogenized in its 4 volumes of PBS. After centrifugation, the supernatants of the extracts were assayed for 2–5AS activity, as described in Experimental Example 3.

Figure 5:
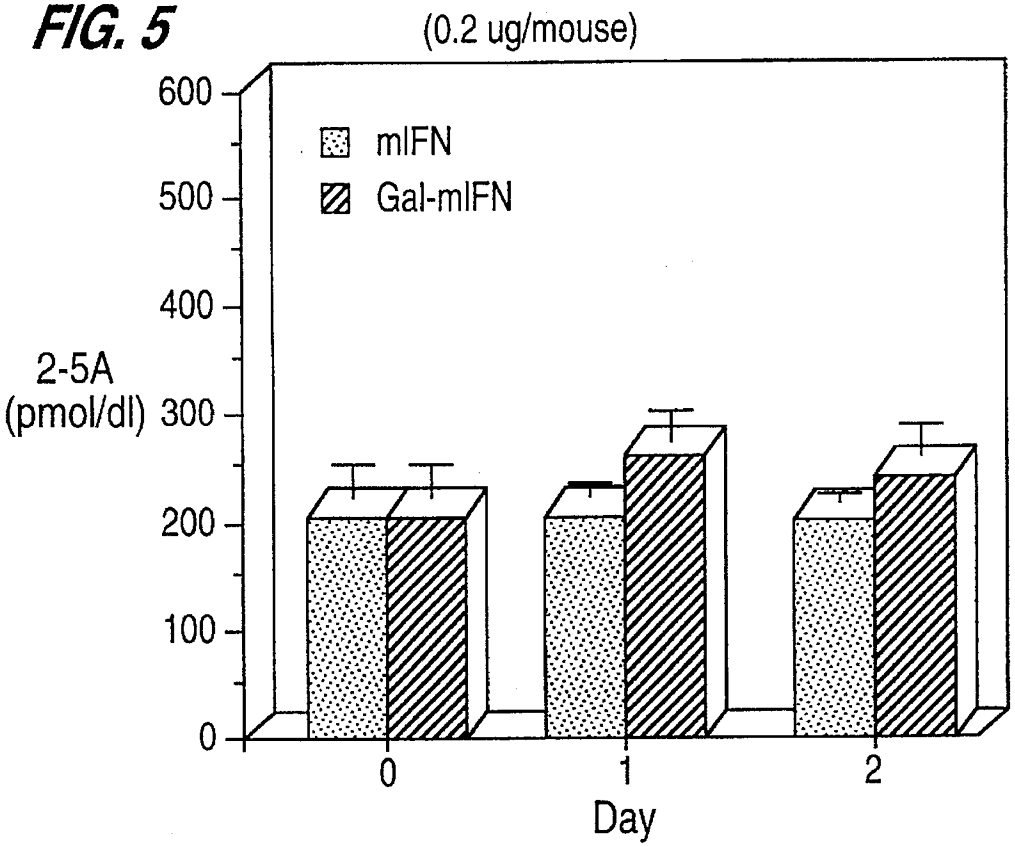
FIG. 5 shows the results of a determination of 2',5'-oligoadenylate (2–5A) synthetase activity in liver following intraperitoneal injections of non-modified interferon-β (IFN β) or galactose-modified IFN β for two consecutive days at a dose of 0.2 μg/day/mouse as IFN β into mice. mIFN and Gal-mIFN show a non-modified mouse IFN β and the galactose-modified mouse IFN β obtained in Example 28, respectively.
Figure 6:
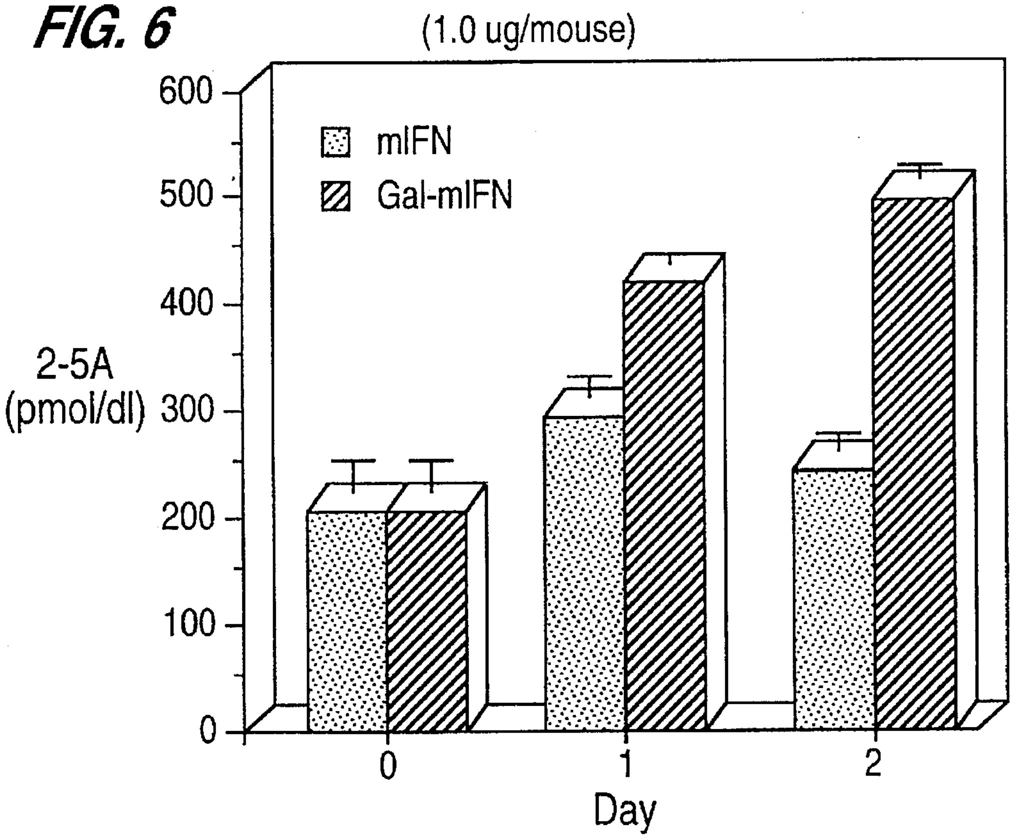
FIG. 6 shows the results of a determination of 2',5'-oligoadenylate (2–5A) synthetase activity in liver following intraperitoneal injections of non-modified interferon-β (IFN β) or galactose-modified IFN β for two consecutive days at a dose of 1.0 μg/day/mouse as IFN β into mice. mIFN and Gal-mIFN show a non-modified mouse IFN β and the galactose-modified mouse IFN β obtained in Example 28, respectively.

The results are given in FIGS. 5 and 6. From FIG. 5, it is seen that the galactose-modified IFN-β raised the 2–5AS activity even at a single dose of 0.2 μg/day/mouse as IFN-β although the non-modified IFN-β did not. From FIG. 6, it is also seen that the galactose-modified IFN-β raised the activity more significantly than the non-modified IFN-β both at a single dose and two consecutive doses of 1.0 μg/day/mouse as IFN-β.

What is claimed is:

1. A sugar-modified interleukin-2 which comprises two to five modifying groups, which may be the same or different, bound to at least one primary amine group of interleukin-2, wherein said modifying group is represented by the formula (I):

R—X— (I)

wherein R represents a glycosyl group;

X represents

—O—CH—CH(OH)—CH(OH)—$CH_2$—
  |
  CH(OH)—$CH_2$OH,

—$C_6H_4$—NH—CS—,

—S—$CH_2$—CO—NH—$CH_2$—$CH_2$—,

—O—$CH_2$—$CH_2$—,

—CS—NH—$C_6H_3(CH_3)$—NHCS—,

—CO—CH(OH)—CH(OH)—CO—,

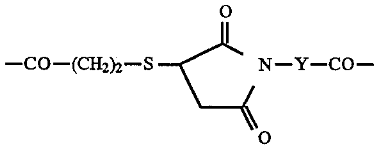

wherein Y is —$(CH_2)_3$—,

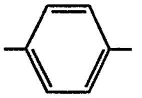 or 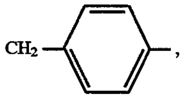,

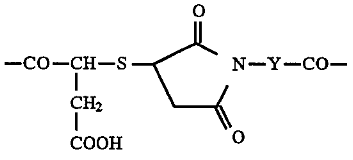

wherein Y is of the same meaning as mentioned above,

—CO—NH— or

—O—CH—CH(OH)—CH(OH)—CO—
  |
  CH(OH)—$CH_2$OH.

2. The sugar-modified interleukin-2 of claim 1 wherein said primary amino group is the ε-amino group of a lysine residue.

3. The sugar-modified interleukin-2 of claim 1 wherein said primary amino group is the α-amino group of the N-terminal amino acid residue.

4. The sugar-modified interleukin-2 of claim 1 wherein said glycosyl group is a glycopyranosyl group.

5. The sugar-modified interleukin-2 of claim 4 wherein said glycopyranosyl group is galactopyranosyl, mannopyranosyl, glucopyranosyl or fucopyranosyl.

6. A pharmaceutical composition comprising a pharmaceutically effective amount of a compound of claim 1 and a pharmaceutically acceptable carrier or diluent.

7. A method of providing an antiviral effect to a mammal by administering to a mammal in need thereof an antiviral effective mount of a composition of claim 6.

8. A method of treating hepatitis by administering to a mammal in need thereof a pharmaceutically effective amount of a composition of claim 6.

9. A sugar-modified interleukin-2 as claimed in claim 1, wherein X is

—O—CH—CH(OH)—CH(OH)—$CH_2$—
  |
  CH(OH)—$CH_2$OH.

10. A sugar-modified interleukin-2 as claimed in claim 1, wherein X is —$C_6H_4$—NH—CS—.

11. A sugar-modified interleukin-2 as claimed in claim 1, wherein X is —S—$CH_2$—CO—NH—$CH_2$—$CH_2$—.

12. A sugar-modified interleukin-2 as claimed in claim 1, wherein X is —O—$CH_2$—$CH_2$—.

13. A sugar-modified interleukin-2 as claimed in claim 1, wherein X is —CS—NH—$C_6H_3(CH_3)$—NHCS—.

14. A sugar-modified interleukin-2 as claimed in claim 1, wherein X is —CO—CH(OH)—CH(OH)—CO—.

15. A sugar-modified interleukin-2 as claimed in claim 1, wherein X is

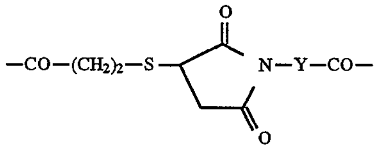

in which Y is —$(CH_2)_3$—

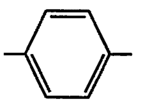 or 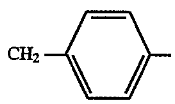.

16. A sugar-modified interleukin-2 as claimed in claim 1, wherein X is

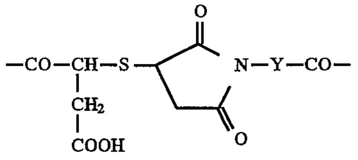

in which Y is —$(CH_2)_3$—

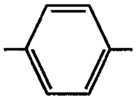 or 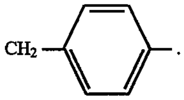

17. A sugar-modified interleukin-2 as claimed in claim 1, wherein X is —CO—NH—.

18. A sugar-modified interleukin-2 as claimed in claim 1, wherein X is

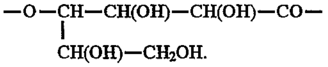

19. A sugar-modified interferon which comprises two to live modifying groups, which may be the same or different, bound to at least one primary amino group of an interferon, wherein said modifying group is represented by the formula (I):

R—X— (I)

wherein R represents a glycosyl group;

X represents

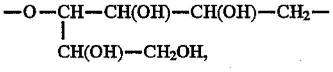

—$C_6H_4$—NH—CS—,

—S—$CH_2$—CO—NH—$CH_2$—$CH_2$—,

—O—$CH_2$—$CH_2$—,

—CS—NH—$C_6H_3(CH_3)$—NHCS—,

—CO—CH(OH)—CH(OH)—CO—,

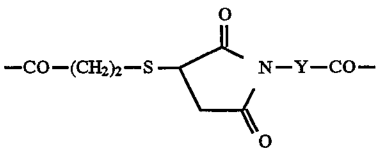

wherein Y is —$(CH_2)_3$—,

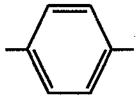 or 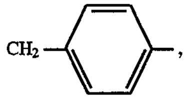,

-continued

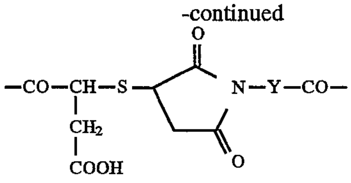

wherein Y is of the same meaning as mentioned above,

—CO—NH— or

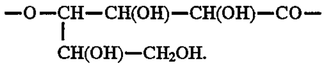

20. The sugar-modified interferon of claim 19 wherein said interferon is interferon-α.

21. The sugar-modified interferon of claim 19 wherein said primary amino group is the ε-amino group of a lysine residue.

22. The sugar-modified interferon of claim 19 wherein said primary amino group is the α-amino group of the N-terminal amino acid residue.

23. The sugar-modified interferon of claim 10 wherein said glycosyl group is a glycopyranosyl group.

24. The sugar-modified interferon of claim 23 wherein said glycopyranosyl group is galactopyranosyl, mannopyranosyl, glucopyranosyl or fucopyranosyl.

25. The sugar-modified interferon of claim 19 wherein four groups represented by formula (I), which may be the same or different, having been bound.

26. A pharmaceutical composition comprising a pharmaceutically effective amount of a compound of claim 19 and a pharmaceutically acceptable carrier or diluent.

27. A method of providing an antiviral effect to a mammal by administering to a mammal in need thereof an antiviral effective amount of a composition of claim 26.

28. A method of treating hepatitis by administering to a mammal in need thereof a pharmaceutically effective amount of a composition of claim 26.

29. A sugar-modified interferon as claimed in claim 19, wherein X is

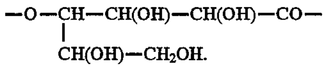

30. A sugar-modified interferon as claimed in claim 19, wherein X is

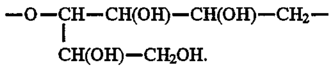

31. A sugar-modified interferon as claimed in claim 19, wherein X is —$C_6H_4$—NH—CS—.

32. A sugar-modified interferon as claimed in claim 19, wherein X is —S—$CH_2$—CO—NH—$CH_2$—$CH_2$—.

33. A sugar-modified interferon as claimed in claim 19, wherein X is —O—$CH_2$—$CH_2$—.

34. A sugar-modified interferon as claimed in claim 19, wherein X is —CS—NH—$C_6H_3(CH_3)$—NHCS—.

35. A sugar-modified interferon as claimed in claim 19, wherein X is —CO—CH(OH)—CH(OH)—CO—.

36. A sugar-modified interferon as claimed in claim 19, wherein X is

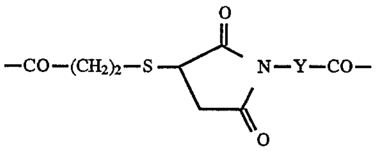
in which Y is $-(CH_2)_3-$
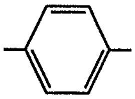 or 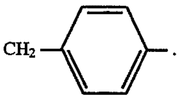.
37. A sugar-modified interferon as claimed in claim 19, wherein X is
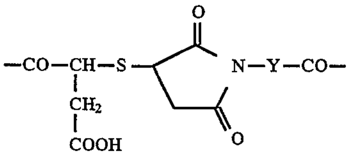
in which Y is $-(CH_2)_3-$
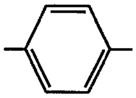 or 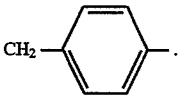.
38. A sugar-modified interferon as claimed in claim 19, wherein X is —CO—NH—.
39. A sugar-modified interferon as claimed in claim 19, wherein X is
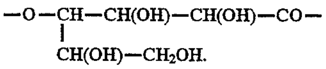
* * * * *

UNITED STATES PATENT AND TRADEMARK OFFICE
CERTIFICATE OF CORRECTION

PATENT NO. : 5,643,564
DATED : July 1, 1997
INVENTOR(S) : HAMAGUCHI et al.

It is certified that error appears in the above-identified patent and that said Letters Patent is hereby corrected as shown below:

In the Claims:

Claim 1, col. 27, line 3, delete "amine group" and insert --amino group--.

Claim 19, col. 29, line 2, delete "live" and insert --five--.

Col. 2, line 12, delete "less" and insert --has--.

Signed and Sealed this

Twentieth Day of January, 1998

Attest:

BRUCE LEHMAN

*Attesting Officer* *Commissioner of Patents and Trademarks*